(12) United States Patent
Ubby et al.

(10) Patent No.: US 7,021,960 B2
(45) Date of Patent: Apr. 4, 2006

(54) MONITORING CABLE

(75) Inventors: Johan Ubby, Vaxholm (SE); Stefan Przetak, Stockholm (SE)

(73) Assignee: Ortivus AB, (SE)

( * ) Notice: Subject to any disclaimer, the term of this patent is extended or adjusted under 35 U.S.C. 154(b) by 0 days.

(21) Appl. No.: 09/899,334

(22) Filed: Jul. 5, 2001

(65) Prior Publication Data

US 2002/0019166 A1 Feb. 14, 2002

Related U.S. Application Data

(60) Provisional application No. 60/216,410, filed on Jul. 6, 2000.

(51) Int. Cl.
*H01R 11/00* (2006.01)

(52) U.S. Cl. ........................... 439/505; 439/624

(58) Field of Classification Search ............... 439/505, 439/909, 624, 502, 623
See application file for complete search history.

(56) References Cited

U.S. PATENT DOCUMENTS

| | | | | | |
|---|---|---|---|---|---|
| 1,574,297 | A | * | 2/1926 | Lilleberg ............... | 439/505 |
| 3,325,765 | A | * | 6/1967 | Hart et al. ............ | 439/505 |
| 3,923,121 | A | * | 12/1975 | Kruppenbach et al. ..... | 439/505 |
| 4,099,824 | A | * | 7/1978 | Schoppelrey ............ | 439/505 |
| 4,353,372 | A | | 10/1982 | Ayer | |
| 4,568,401 | A | * | 2/1986 | Davis ................. | 439/502 |
| 4,686,998 | A | * | 8/1987 | Robbins .............. | 128/670 |
| 4,890,630 | A | * | 1/1990 | Kroll et al. ........... | 128/901 |
| 5,176,535 | A | * | 1/1993 | Redmond et al. ........ | 439/495 |
| 5,236,374 | A | * | 8/1993 | Leonard et al. ......... | 439/505 |
| 5,515,848 | A | | 5/1996 | Corbett, III et al. | |
| 5,546,950 | A | * | 8/1996 | Schoeckert et al. ...... | 439/505 |
| 5,601,448 | A | * | 2/1997 | Poon ................. | 439/505 |

FOREIGN PATENT DOCUMENTS

EP 481290 A1 4/1992

* cited by examiner

*Primary Examiner*—Tho D. Ta
*Assistant Examiner*—Felix O. Figueroa
(74) *Attorney, Agent, or Firm*—Cooper & Dunham LLP

(57) ABSTRACT

A monitoring cable includes a cable including plurality of individual wires each extending substantially an entire length of the monitoring cable and a plurality of electrodes each electrically connected to a respective one of the plurality of individual wires and positioned at various points along the cable.

41 Claims, 9 Drawing Sheets

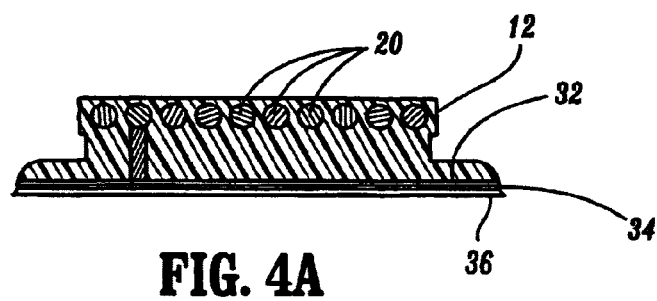
FIG. 4A
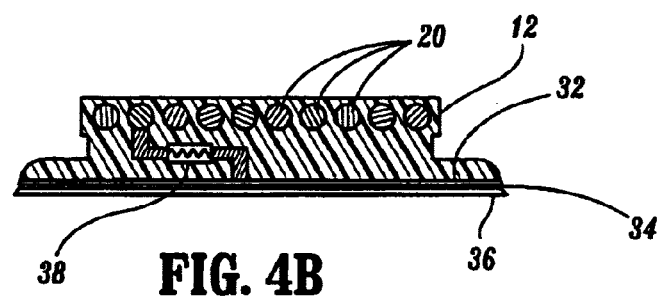
FIG. 4B
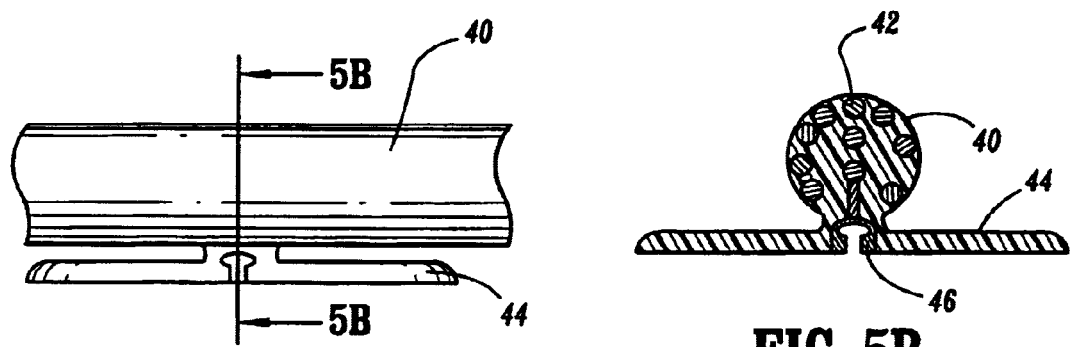
FIG. 5A          FIG. 5B
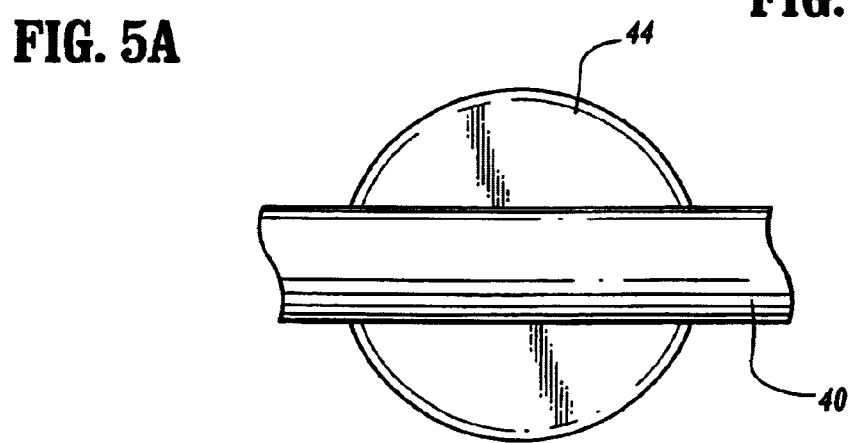
FIG. 5C

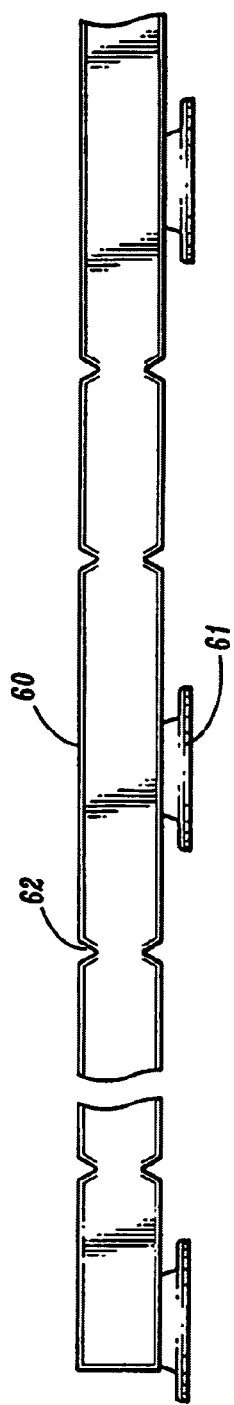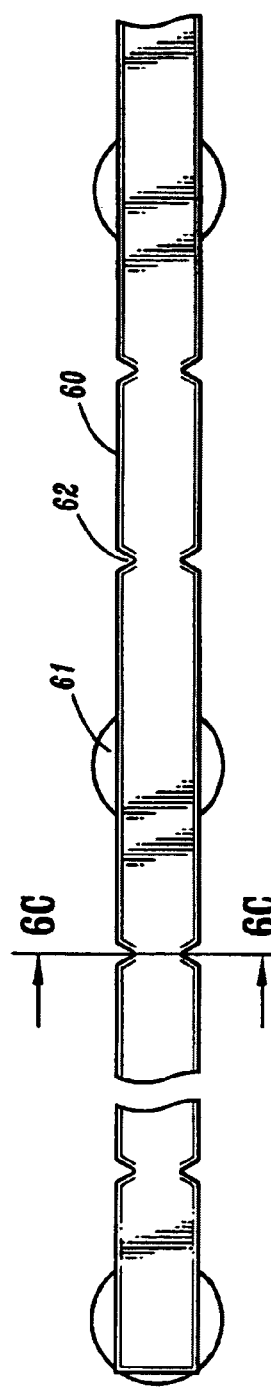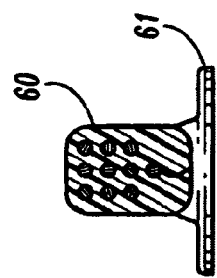

MONITORING CABLE

CROSS REFERENCE TO RELATED APPLICATION

This application is based on Provisional Application Ser. No. 60/216,410 filed Jul. 6, 2000, the entire contents of which are herein incorporated by reference.

BACKGROUND OF THE DISCLOSURE

1. Field of the Disclosure

The present disclosure relates to monitoring cables and, more specifically, to monitoring cables in which electrodes or electrode connectors are provided along the cable.

2. Description of the Related Art

An electrocardiogram (ECG) is used when monitoring a patients heart activity. A patient is connected to an ECG monitoring system with ECG cables. A typical ECG cable for monitoring, for example, is referred to as a 12-lead ECG. A 12-lead ECG requires the use of a 10 wire ECG cable for acquiring ECG signals. One end of the cable is connected to a monitor/acquisition unit with a trunk cable via a connector. The other end of the trunk cable includes a splitter. The splitter splits the 10 individual lead wires provided in the trunk cable, into the 10 lead wires to be connected to the patient. Each of the 10 lead wires is typically 1 m long. Other types of monitor cables include 3, 5 and 8 wire cables.

A problem with such ECG cables is that they are very cumbersome to connect to the patient, particularly when using a 10-wire ECG cable for 12-lead ECG monitoring. In addition, the lead wires tend to tangle, further making use of the ECG cable difficult. It can be difficult for the user to untangle the lead wires while at the same time trying to connect the correct lead wire to the corresponding electrode on the patient. The procedures for connecting the typical ECG cable are time consuming and are not very user friendly.

SUMMARY

A monitoring cable includes a cable including plurality of individual wires each extending substantially an entire length of the monitoring cable and a plurality of electrodes each electrically connected to a respective one of the plurality of individual wires and positioned at various points along the cable. According to another aspect of the disclosure, a monitoring cable includes a cable including plurality of individual wires each extending substantially an entire length of the cable and a plurality of electrode connectors each electrically connected to a respective one of the plurality of wires and positioned at various points along the cable.

The plurality of individual wires may each comprise single strands of wire or multi-strand wires. The plurality of electrodes or electrode connectors may be integrally formed in the cable. The monitoring cable may further include a plurality of resistive elements each electrically positioned between an electrode connector and its respective one of the plurality of wires. The cable may be a substantially flat ribbon cable, the plurality of individual wires extending side by side substantially the entire length of the monitoring cable. The cable may be substantially circular in cross section. The plurality of individual wires are electrically insulated from each other. An interface connector may be provided at one end of the cable and including a plurality of contact portions each connected to a respective one of the plurality of individual wires, the interface connector provided for connecting the monitoring cable to monitoring equipment.

According to another aspect of the present disclosure, a monitoring cable includes a plurality of respective cables, each of the plurality of respective cables including plurality of individual wires each extending substantially an entire length of the respective cable. A plurality of electrodes or electrode connectors are each electrically connected to a respective one of the plurality of individual wires and positioned at various points along each of the plurality of respective cables.

SUMMARY OF THE DRAWINGS

A more complete appreciation of the present embodiments and many of the attendant advantages thereof will be readily obtained as the same becomes better understood by reference to the following detailed description when considered in connection with the accompanying drawings, wherein:

FIGS. 4A, 4B show cross-sectional views of a cable according to another embodiment and including an integrally molded electrode pad without and with a protective resistor, respectively;

FIG. 5A is a partial side view of an ECG cable according to another embodiment;

FIG. 5B is a cross-sectional view, taken along lines 5B—5B in FIG. 5A;

FIG. 5C is a partial top view of the cable shown in FIG. 5A;

FIG. 6A is a partial side view of an ECG cable according to another embodiment, FIG. 6B is a top view of FIG. 6A and FIG. 6C is a cross-sectional view taken along lines 6C—6C in FIG. 6B;

DESCRIPTION OF THE PREFERRED EMBODIMENTS

Figure 1A:
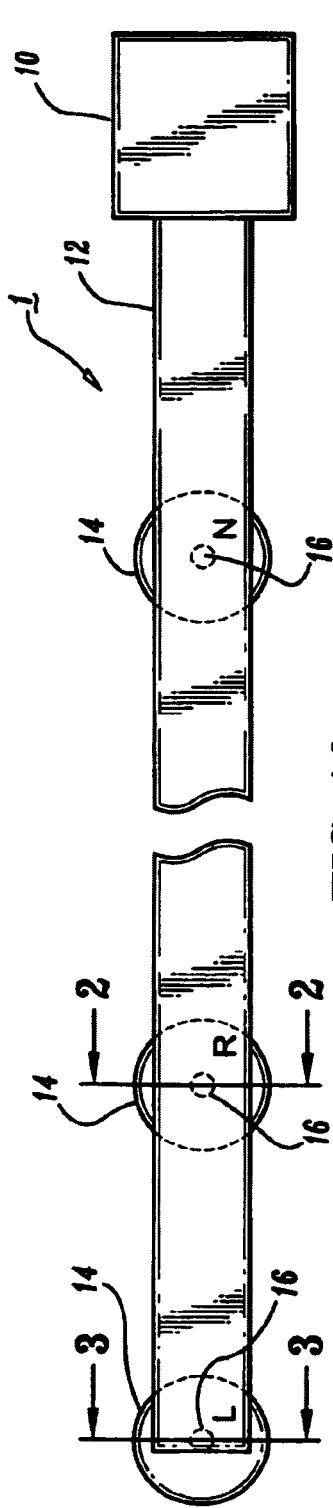
FIGS. 1A–1D show a partial top view, partial bottom view, partial side view and full perspective view, respectively, of a 12-lead ECG cable according to an embodiment.

In describing preferred embodiments of the present disclosure illustrated in the drawings, specific terminology is employed for sake of clarity. However, the present disclosure is not intended to be limited to the specific terminology so selected and it is to be understood that each specific element includes all technical equivalents which operate in a similar manner.

Figure 1B:
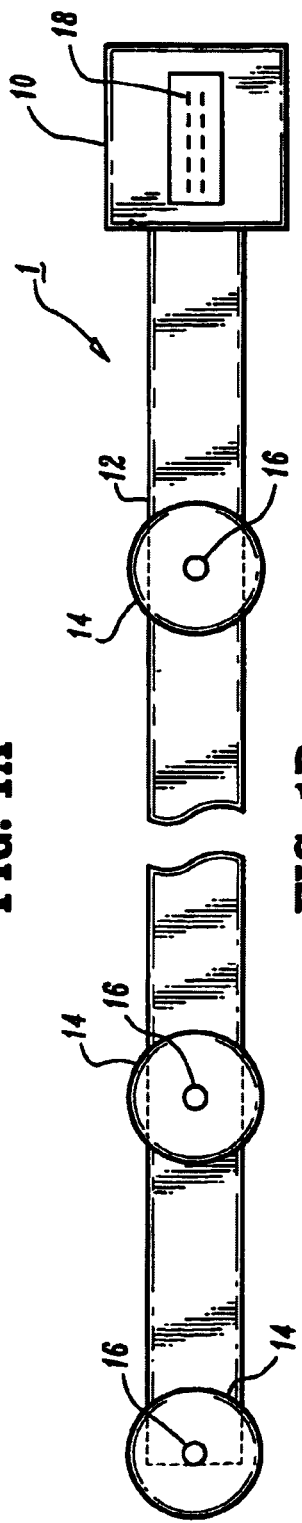
Figure 1C:
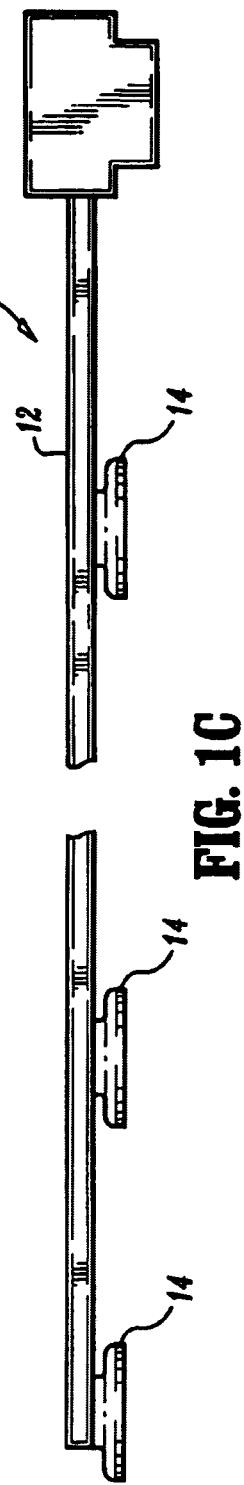

Referring to FIGS. 1A–1C there is shown an ECG cable according to a first embodiment, referred to generally as ECG cable 1. The following embodiments will be described with reference to a 10-wire ECG cable for performing 12-lead monitoring. However, it should be understood that any number of wires may be embodied herein.

Figure 1D:
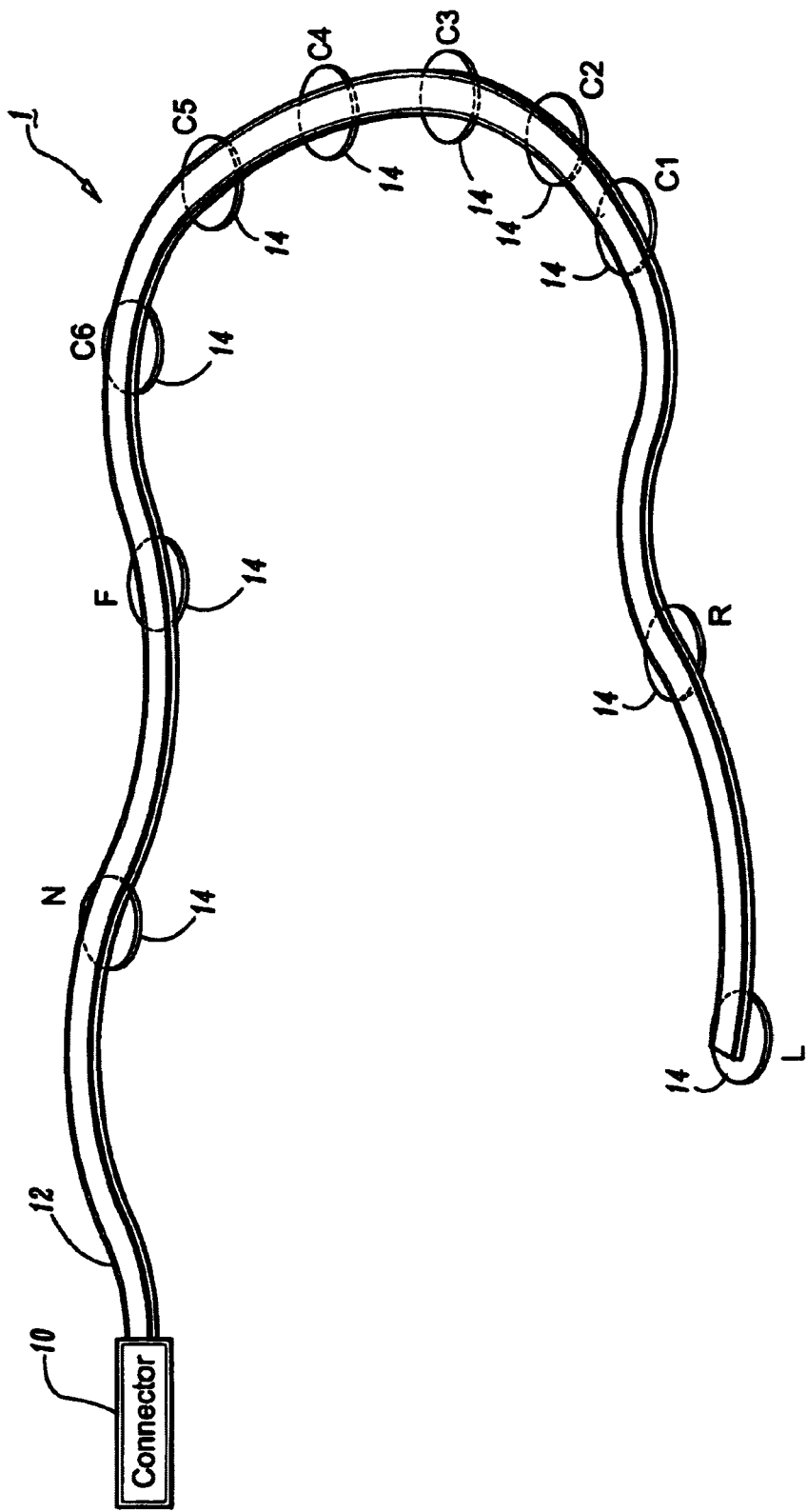

ECG cable 1 includes cable portion 12, ten electrode contact portions 16 and monitor connector 10 including contacts 18. Monitor connector 10 is a standard type connector suitable for connecting to a piece of monitoring equipment. According to this embodiment, cable portion 12 is a flat ribbon cable including ten individual wires provided therein, each of which extends the entire length of the cable 12. Molded integrally into the ribbon cable 12 are ten electrode contacts 16. Each electrode contact 16 is electrically connected to a corresponding one of the wires in ribbon cable 12. That is, as shown in FIG. 1D, electrode contacts for connecting ten electrodes, N, F, C6–C1, R and L are provided. Each of the electrode contacts is electrically connected to one of corresponding wires in cable 12. Each of the ten wires extend the entire length of the cable 12 for providing a strong yet flexible cable for its entire length. As shown in FIG. 1A, the ribbon cable 12 (or the electrode pads 14) may be marked indicating the position on the patient each electrode contact portion is to be placed.

Figure 1E:
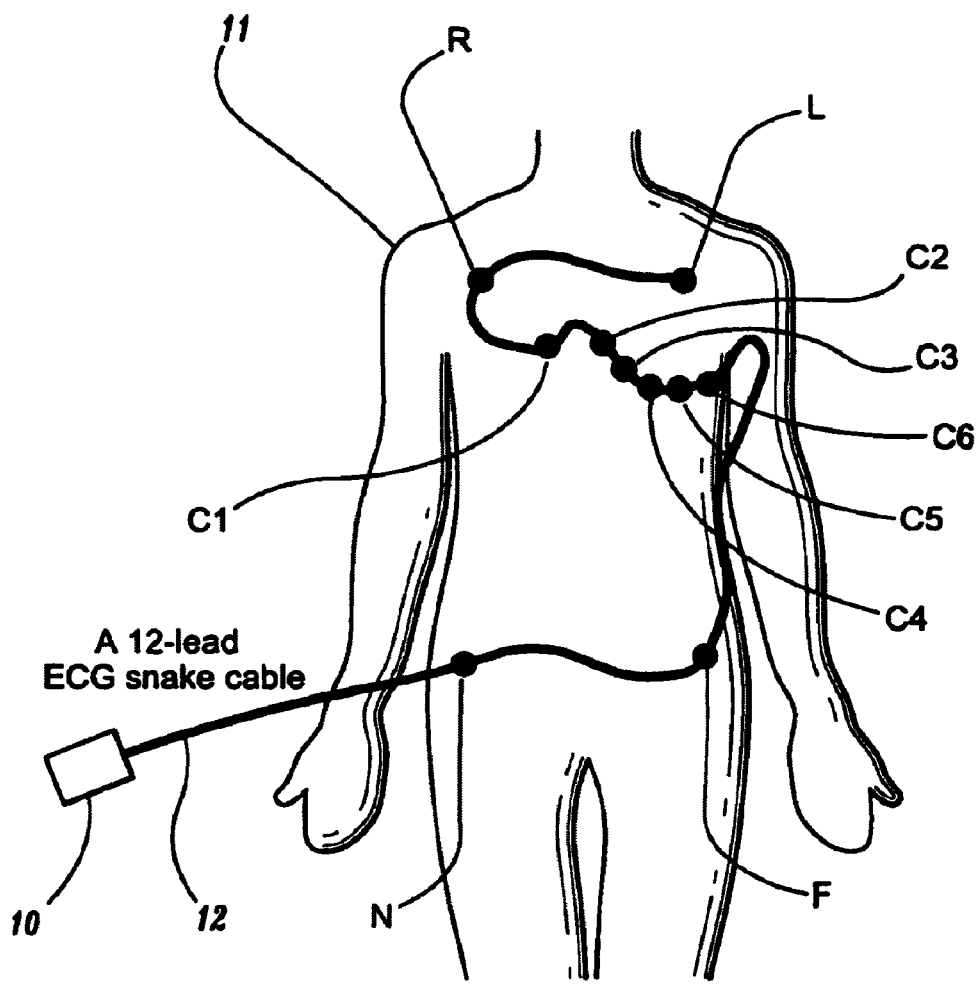
FIG. 1E shows placement of the ECG cable shown in FIGS. 1A–1D.

Placement of the cable/electrodes on a patient 11 is shown in FIG. 1E. Pad R is placed on the right side on the superior part of the patient's chest. Pad L is placed on the left side on the superior part of the patient's chest. Pads C1–C2 are placed on the right respectively left side sternum at the same level as the $4^{th}$ intercostal space. C3 is placed between C2 and C4. C4 is placed on the $5^{th}$ intercostal space in the middle clavicular line. C5–C6 is placed at the same level as C4 in the anterior respectively middle axillar line. N is placed on the right hipbone and F is placed on the left hipbone of the patient. Of course, placement of the cable/electrodes on the patient may be at different positions if desired.

Figure 2A:
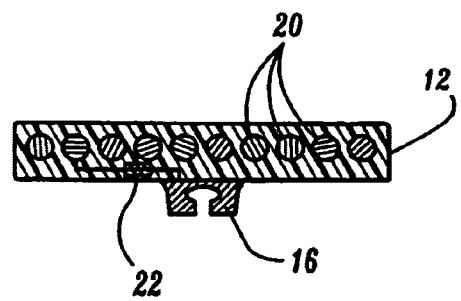
FIG. 2A shows a cross-sectional view taken along lines 2—2 in FIG. 1A including a protective resistor according to an embodiment.

FIG. 2A is a cross-section of ECG cable 1 according to an embodiment, taken along lines 2—2 in FIG. 1A. As shown, each electrode contact 16 is molded integrally with ribbon cable 12. According to the embodiments described herein, the electrode contacts 16 are "snap" type contacts. The "snap" type contacts allow electrode pads 14 (FIG. 2B) to be easily connected to and removed from the electrode contacts 16 or the ECG cable 1. Of course, other types of electrode contacts are contemplated.

Figure 2B:
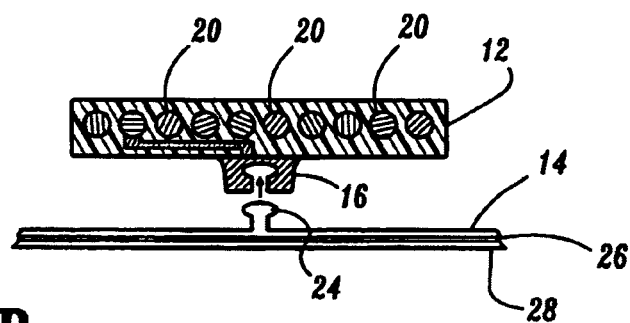
FIG. 2B shows a cross-sectional view taken along lines 2—2 in FIG. 1A without a protective resistor according to another embodiment.

Ribbon cable 12 includes ten (10) individual wires 20 each of which extends the length of cable 12. Since each wire 20 extends the length of cable 12 from connector 10 to the distal end of the cable, the cable is durable, flexible and easy to manufacture. As shown in FIG. 2A, electrode contact 16 may be connected to its respective wire 20, via a surge protective resistor 22 which may be integrally formed in the connector 16 or in ribbon cable 12. As shown in FIG. 2B, if a surge protective resistor is not used, or is provided elsewhere within cable 12 or connector 10, each electrode contact 16 is connected directly to its corresponding wire 20. Electrode pad assembly 14 (FIG. 2B) includes a contact post portion 24 dimensioned to snap-fit within electrode contact 16. Electrode pad assembly 14 includes a release sheet 28 covering adhesive 26.

Figure 3A:
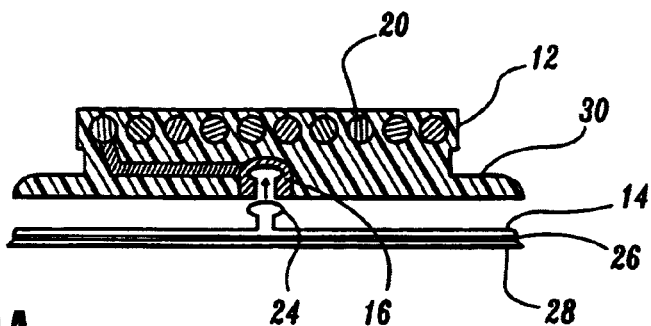
FIGS. 3A, 3B show cross-sectional views taken along lines 3—3 in FIG. 1A without and with a protective resistor, respectively.
Figure 3B:
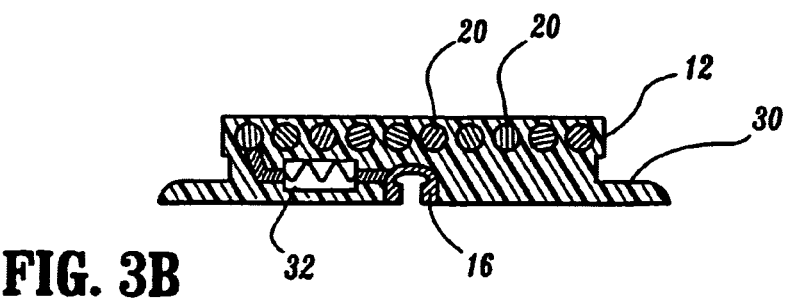

According to another embodiment as shown in FIG. 3A, a pad base 30 may be molded integrally into the bottom of ribbon cable 12 to provide additional support for electrode pad assembly 14. As shown in FIG. 3B, a surge protective resistor 32 may be integrally formed in the pad base 30. Pad base 30 may be dimensioned roughly the same diameter as electrode pad assembly 14.

According to yet another embodiment, the electrode pad assembly may itself be formed integrally with the ribbon cable 12. As shown in FIGS. 4A and 4B, electrode pad 32 is provided integral with the ribbon cable 12. Reusable adhesive 34 and release sheet 36 are also provided. As shown in FIG. 4B, a surge protective resistor 38 may be provided.

Instead of a ribbon cable, other types and shapes of cables may be used. According to the embodiment as shown in FIGS. 5A–5C, a round cable 40 (only a small portion of which is shown) including a plurality of conductors 42 may be used in place of ribbon cable 12. Each electrode connector 46 is electrically connected to a corresponding conductor 42 within cable 40. As with the ribbon cable described above, conductors 42 extend the length of the cable. Electrode pad support 44 is molded integrally with cable 40. An electrode pad (not shown) similar to pad 14 shown in FIGS. 2B, 3A, for example, may then be snap-fit into electrode connector 46.

Figure 5D:
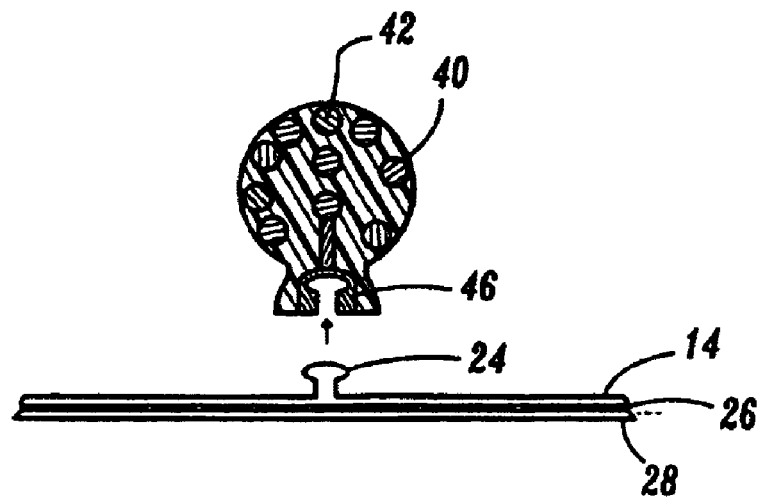
FIGS. 5D, 5E are cross-sectional views depicting different embodiments for electrode placement.
Figure 5E:
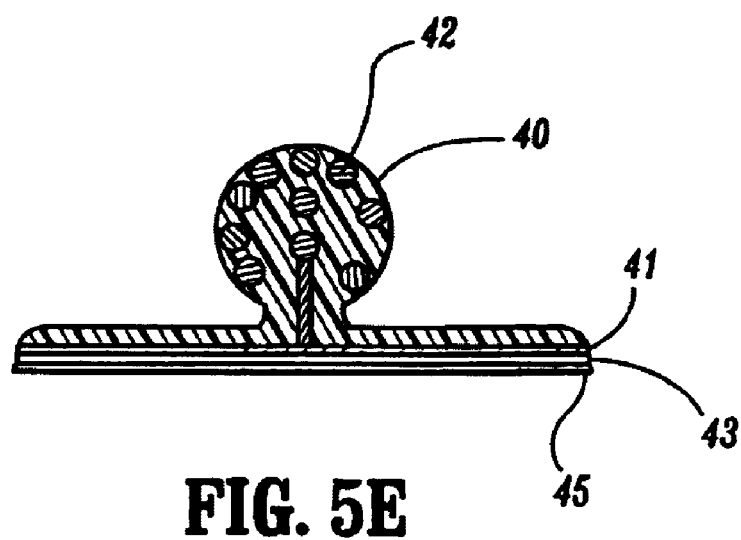

In an alternative embodiment as shown in FIG. 5D, the electrode pad support 44 can be omitted with just the electrode connector 46 being integrally molded with cable 40. In another embodiment as shown in FIG. 5E, the electrode pad 41 itself can be integrally molded with the cable 40, similar to that shown in FIGS. 4A, 4B. Electrode pad 41 includes reusable adhesive 43 covered by release sheet 45. Of course, surge protective resistors (not shown) may be provided in each of the disclosed embodiments.

Another embodiment is shown in FIGS. 6A–6C. In this embodiment, cable 60 includes a series of notches 62 formed therein, which give the cable additional flexibility. The notches may extend completely around the cable or may extend only along the sides or a portion thereof, depending on the amount of flexibility desired. Electrode pad 61 may be integrally formed with cable 60. In the alternative, snap-fit connectors (not shown) may be formed integrally with the cable 60 and an electrode pad (not shown) similar to pad 14 shown in FIGS. 2B, 3A snap-fit therein.

Figure 7A:
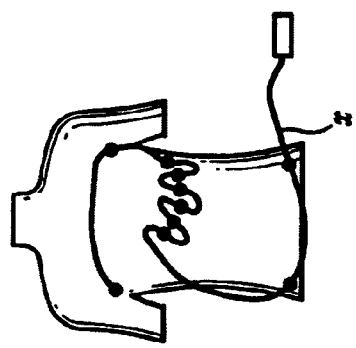
FIGS. 7A–7C show a 12-Lead ECG with one cable, two cables and three cables, respectively.
Figure 7B:
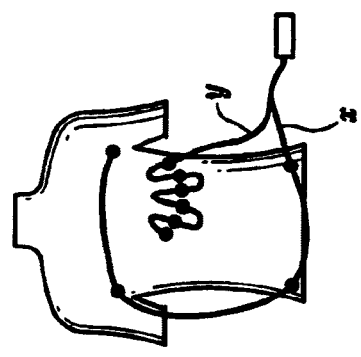
Figure 7C:
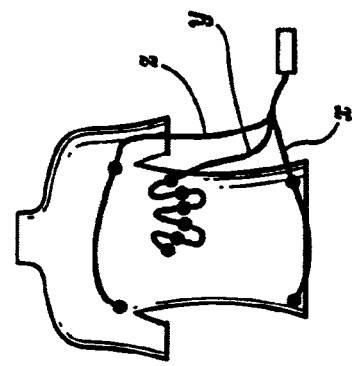

Variations of the above-described embodiments are possible. For example, as described above, all electrodes can be provided on one cable (x) as shown in FIG. 7A which shows a 12-lead, one cable configuration. In an alternative embodiment shown in FIG. 7B, which depicts a 12-lead, two cable configuration, four of the electrodes can be provided on one cable (x), with four wires extending the length of that cable. The six remaining electrodes can then be provided in another cable (y), with six wires extending the length of that cable. In another embodiment, three individual cables can be provided as shown in FIG. 7C, which depicts a 12-lead, three cable configuration, grouping the electrodes for easy and convenient placement on a patients chest. In this embodiment the three cables (x, y, z, respectively) would have two, six and two wires extending the lengths thereof, respectively.

Figure 8A:
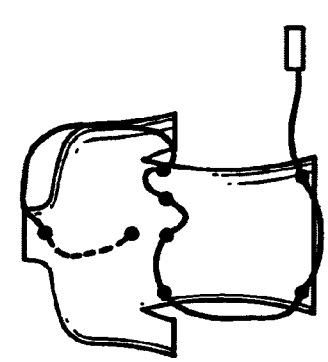
FIGS. 8A–8C show 8 wire VCG with one cable, two cables and three cables, respectively.
Figure 8B:
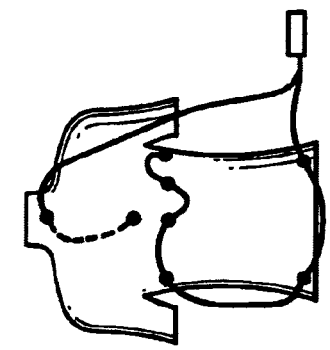
Figure 8C:
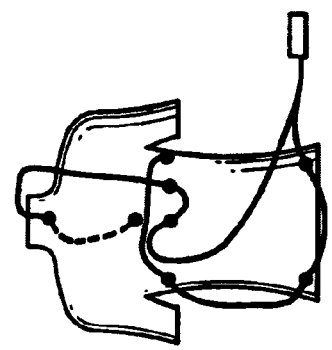

As shown in FIGS. 8A–8C, a cable for use in an 8 wire VCG system (Frank lead system) can include one cable (FIG. 8A), two cables (FIG. 8B) or three cables (FIG. 8C). Of course, more cables may be provided if desired.

According to an embodiment, the above-described cables can be shielded and the cable and/or electrode/electrode connectors can be clearly marked indicating position on the patient to which it is to be placed.

According to yet another embodiment, the shape of the ribbon cable or the diameter of the round cable remains the same for the entire length thereof. However, in this embodiment, the wires for connecting to the electrodes do not extend the entire length of the cable. Instead, each wire terminates at the corresponding electrode or electrode connector. Since the shape or diameter of the cable remains the same for the length thereof, the cable is durable yet flexible. In another embodiment, if two or more cables are used (see, for example, FIGS. 8B, 8C), the diameter or width of each cable may be different and the diameter or width of each respective cable may remain the same for its entire length, with the wires terminating at their respective electrodes.

Figure 9:
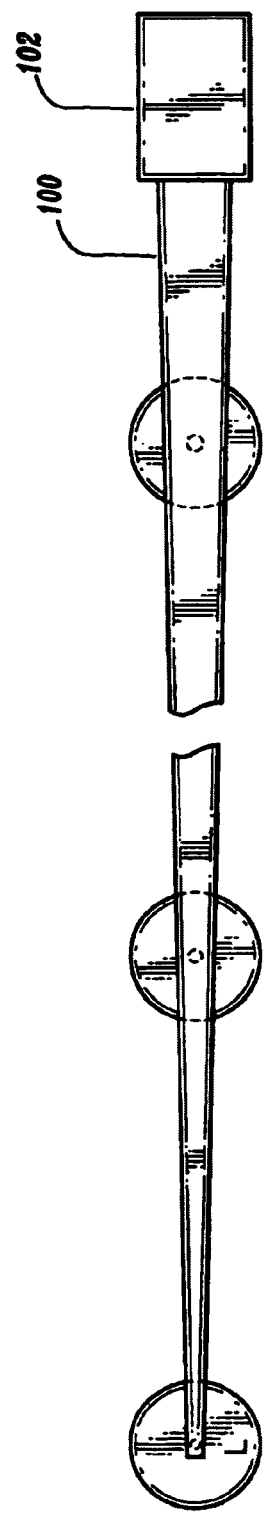
FIG. 9 shows a partial top view of an ECG cable according yet another embodiment.

According to still another embodiment, each wire terminates at the corresponding electrode or electrode connector. However, as shown in FIG. 9, in this embodiment, the ribbon cable 100 tapers in width from the widest portion being attached to the monitor connector 102 to the narrowest width provided at the distal end. The distal end being the end having the electrode connector "L" provided thereon, for example, as shown. In a similar manner, if a round cable is preferred and each wire terminates at the corresponding electrode or electrode connector, the cable tapers from a largest diameter section attached at the monitor connector down to the smallest diameter section at the distal end. In another embodiment, if two or more cables are used (see, for example, FIGS. 8B, 8C), the diameter or width of each cable may taper from its widest end connected to the monitor connector, to the narrowest width provided at the distal end, with the wires terminating at their respective electrodes.

Although the descriptions herein may refer to particular standard designations when referring to relevant terms, it should be clear that the present embodiments are in no way limited by the particular standards used to describe the embodiments. For example, although the leads are described using reference to the IEC standard, it should be clear that the disclosure is in no way limited to that standard. For example, an ANSI standard could be substituted for the IEC standard terminology.

According to the embodiments described herein, a convenient user-friendly ECG cable can be provided which allows the electrodes to be quickly and easily placed on the patient. Tangling lead wires is drastically reduced, misplacement of lead wires on the patient is reduced and the time required to connect the ECG cable is reduced.

Numerous additional modifications and variations of the present embodiments are possible in view of the above-teachings. It is therefore to be understood that within the scope of the appended claims, the present embodiments may be practiced other than as specifically described herein.

What is claimed is:

1. A monitoring cable comprising:
   a connector for connection to a monitoring equipment,
   a cable including a plurality of individual wires each extending substantially an entire length of the cable, the cable having a first end to which the connector is attached and a distal end; and
   a plurality of electrodes each electrically connected to a respective one of the plurality of individual wires and positioned at various points along the cable, each of the plurality of electrodes being electrically isolated from each of the other plurality of electrodes, at least one of the plurality of electrodes being positioned between the first end and the distal end.

2. A monitoring cable as recited in claim 1, wherein the plurality of individual wires each comprise single strands of wire.

3. A monitoring cable as recited in claim 1, wherein the plurality of individual wires each comprise multi-strand wires.

4. A monitoring cable as recited in claim 1, wherein the plurality of electrodes are integrally formed in the cable.

5. A monitoring cable as recited in claim 1, further comprising a plurality of resistive elements each electrically positioned between a respective electrode and the respective one of the plurality of wires.

6. A monitoring cable as recited in claim 1, wherein the cable is a substantially flat ribbon cable, the plurality of individual wires extending side by side substantially the entire length of the monitoring cable.

7. A monitoring cable as recited in claim 1, wherein the cable is substantially circular in cross section.

8. A monitoring cable as recited in claim 1, wherein the plurality of individual wires are electrically insulated from each other.

9. A monitoring cable as recited in claim 1, wherein the connector comprises an interface connector provided at one end of the cable and including a plurality of contact portions each connected to a respective one of the plurality of individual wires, the interface connector provided for connecting the monitoring cable to the monitoring equipment.

10. A monitoring cable as recited in claim 1, wherein each of the at least one electrodes are positioned between the first end and the distal end of the cable for placement at specific positions on a patient.

11. A monitoring cable comprising:
    a cable including a plurality of individual wires each extending substantially an entire length of the cable; and
    a plurality of electrode connectors each electrically connected to a respective one of the plurality of wires and positioned at various points along the cable, each of the plurality of electrode connectors being electrically isolated from each of the other of the plurality of electrode connectors at least one of the plurality of electrode connectors being positioned between a first and a distal end of the cable.

12. A monitoring cable as recited in claim 11, wherein the plurality of individual wires each comprise single strands of wire.

13. A monitoring cable as recited in claim 11, wherein the plurality of individual wires each comprise multi-strand wires.

14. A monitoring cable as recited in claim 11, wherein the plurality of electrode connectors are integrally formed in the cable.

15. A monitoring cable as recited in claim 11, further comprising a plurality of resistive elements each electrically positioned between a respective electrode connector and the respective one of the plurality of wires.

16. A monitoring cable as recited in claim 11, wherein the cable is a substantially flat ribbon cable, the plurality of wires extending side by side substantially the entire length of the monitoring cable.

17. A monitoring cable as recited in claim 11, wherein the cable is substantially circular in cross section.

18. A monitoring cable as recited in claim 11, wherein the plurality of individual wires are electrically insulated from each other.

19. A monitoring cable as recited in claim 11, further comprising an interface connector provided at one end of the cable and including a plurality of contact portions each connected to a respective one of the plurality of individual wires, the interface connector provided for connecting the monitoring cable to monitoring equipment.

20. A monitoring cable as recited in claim 11, wherein each of the at least one electrode connectors are positioned at specific points along the cable for connection to electrodes attached at specific positions on a patient.

21. A monitoring cable comprising:
a connector for connection to a monitoring equipment;
a plurality of respective cables, each of the plurality of respective cables including plurality of individual wires each extending substantially an entire length of the respective cable, each of the plurality of individual wires of each of the plurality of respective cables having an end terminating at the connector; and
a plurality of electrodes each electrically connected to a respective one of the plurality of individual wires and positioned at various points along each of the plurality of respective cables, each of the plurality of electrodes being electrically isolated from each of the other of the plurality of electrodes at least one of the plurality of electrodes being positioned between a first and a distal end of the cable.

22. A monitoring cable as recited in claim 21, wherein each of the at least one of the plurality of electrodes are positioned at specific points along its respective cable for placement at specific positions on a patient.

23. A monitoring cable comprising:
a connector for connection to a monitoring equipment;
a plurality of respective cables, each of the plurality of respective cables including a plurality of individual wires each extending substantially an entire length of the respective cable, each of the plurality of individual wires of each of the plurality of respective cables having an end terminating at the connector; and
a plurality of electrode connectors each electrically connected to a respective one of the plurality of individual wires and positioned at various points along each of the plurality of respective cables, each of the plurality of electrode connectors being electrically isolated from each of the other of the plurality of electrode connectors at least one of the plurality of electrode connectors being positioned between a first and a distal end of the cable.

24. A monitoring cable as recited in claim 23, wherein each of the at least one of the plurality of electrode connectors are positioned at specific points along its respective cable for connection to electrodes attached at specific positions on a patient.

25. A monitoring cable comprising:
a cable including a plurality of individual wires each extending substantially an entire length of the cable, the cable having substantially a same shape for substantially an entire length thereof; and
a plurality of electrodes each electrically connected to a respective one of the plurality of individual wires and positioned at various points along the cable, each of the plurality of electrodes being electrically isolated from each of the other of the plurality of electrodes at least one of the plurality of electrodes being positioned between a first and a distal end of the cable.

26. A monitoring cable as recited in claim 25, wherein the plurality of individual wires each comprise single strands of wire.

27. A monitoring cable as recited in claim 25, wherein the plurality of individual wires each comprise multi-strand wires.

28. A monitoring cable as recited in claim 25, wherein the plurality of electrodes are integrally formed in the cable.

29. A monitoring cable as recited in claim 25, further comprising a plurality of resistive elements each electrically positioned between a respective electrode and the respective one of the plurality of wires.

30. A monitoring cable as recited in claim 25, wherein the cable is a substantially flat ribbon cable, the plurality of individual wires extending side by side.

31. A monitoring cable as recited in claim 25, wherein the cable is substantially circular in cross section.

32. A monitoring cable as recited in claim 25, wherein the plurality of individual wires are electrically insulated from each other.

33. A monitoring cable as recited in claim 25, further comprising an interface connector provided at one end of the cable and including a plurality of contact portions each connected to a respective one of the plurality of individual wires, the interface connector provided for connecting the monitoring cable to monitoring equipment.

34. A monitoring cable as recited in claim 25, wherein the shape comprises at least one of a width and diameter of the cable.

35. A monitoring cable as recited in claim 25, wherein each of the plurality electrodes is positioned at specific points along the cable for placement at specific positions on a patient.

36. A monitoring cable comprising:
a connector for connection to a monitoring equipment;
a plurality of respective cables, each of the plurality of respective cables including plurality of individual wires, each wire extending substantially an entire length of the cable, each respective cable having a shape, each respective cable having substantially a same shape for substantially an entire length thereof, each of the plurality of wires of each of the plurality of respective cables having an end terminating at the connector; and
a plurality of electrodes each electrically connected to a respective one of the plurality of individual wires and positioned at various points along each of the plurality of respective cables, each of the plurality of electrodes being electrically isolated from each of the other of the plurality of electrodes at least one of the plurality of electrodes being positioned between the end and a distal end of the cable.

37. A monitoring cable as recited in claim 36, wherein the shape comprises at least one of a width and diameter of the cable.

38. A monitoring cable as recited in claim 36, wherein each of the plurality of electrodes are positioned at specific points along its respective cable for placement at specific positions on a patient.

39. A monitoring cable comprising:
a plurality of respective cables, each of the plurality of respective cables including a plurality of individual wires, each wire extending substantially an entire length of the cable, each respective cable having a shape, each respective cable having substantially a same shape for substantially an entire length thereof, each of the plurality of wires of each of the plurality of respective cables having an end terminating at a connector; and
a plurality of electrode connectors each electrically connected to a respective one of the plurality of individual wires and positioned at various points along each of the plurality of respective cables, each of the plurality of electrode connectors being electrically isolated from each of the other of the plurality of electrode connectors at least one of the plurality of electrode connectors being positioned between the end and a distal end of the cable.

40. A monitoring cable as recited in claim 39, wherein the shape comprises at least one of a width and diameter of the cable.

41. A monitoring cable as recited in claim 39, wherein each of the plurality of electrode connectors are positioned at specific points along its respective cable for connection to electrodes attached at specific positions on a patient.

* * * * *